Nov. 11, 1952 A. P. HOWARD Plant Pat. 1,145
ROSE PLANT
Filed Dec. 13, 1951
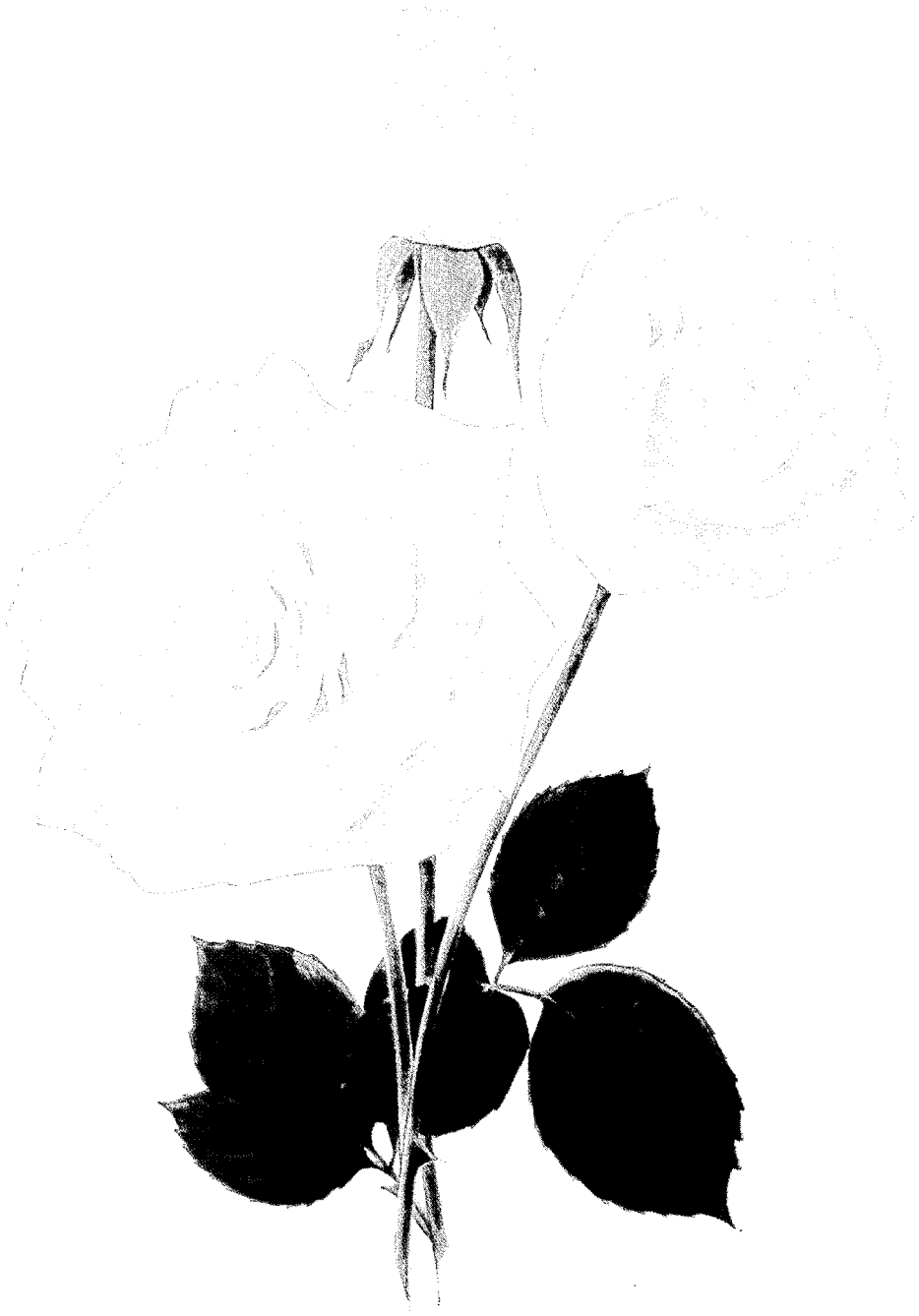
INVENTOR
Arthur Preston Howard
By Orville M. Kile
Plant Pat. Agent Patented Nov. 11, 1952

Plant Pat. 1,145

UNITED STATES PATENT OFFICE 1,145

ROSE PLANT

Arthur Preston Howard, Sierra Madre, Calif., assignor to Howard & Smith, Montebello, Calif.

Application December 13, 1951, Serial No. 261,515

1 Claim. (Cl. 47—61)

My invention pertains to a new and distinct variety of hybrid tea rose plant of the novelty type and its principal points of novelty are in its flower coloring, keeping qualities and stem strength.

My new variety is the result of definite breeding efforts conducted by me at greenhouses in southern California and is the product of a cross between the variety Fred Howard (Plant Patent No. 1006) and one of our unnamed seedlings. I have asexually reproduced this new variety at the same location, by means of budding, and its characteristics appear to be permanent.

The accompanying illustration shows three specimens of this rose in approximately their true colors, together with portions of the stems and foliage.

Varieties known to me which are most like my new variety are Peace (Plant Patent #591) and one of its parents, Fred Howard (Plant Patent No. 1006). Principal differences from these varieties are its stronger stems, better keeping qualities, and more intense coloring in regard to both the principal color and the pink tinting.

In the following detail description, color plate reference indicate Ridgway's Color Standards and Nomenclature.

*The plant*

Growth habit: Strong, vigorous, upright bush.

Blooming habit: Very floriferous. Produces large quantity of good blooms throughout the season from early spring to late fall.

Stems: Moderately heavy and very strong. Attain 18 inches or more in length. Approximately Calla Green (Pl. V), tinged with Oxblood Red (Pl. I).

*Thorns.*—Medium size, approximately ¼ inch long; outward-pointing; usually overlaid with Oxblood Red; found mostly on lower portion of stem.

Foliage:

*Type.*—Pinnately compound, with 5 to 7 leaflets.

*Shape.*—Leaflets oval, with acuminate apex and usually rounded base. Edge sharply serrated.

*Size.*—Terminal leaflet 1 to 1¼ inches in length and ¾ to 1 inch wide, with lateral leaflets smaller but still of good size.

*Quantity.*—Normal.

*Texture.*—Leathery.

*Color.*—Forest Green to Elm Green (Pl. XVII).

*Rachis.*—Heavy; grooved and red-tinged above; under side with a few small thorns.

*Stipules.*—Long; narrow; clinging; moderately long points extending outward.

*The flower*

Bud:

*Shape.*—Semi-globose, opening somewhat urnshaped.

*Size.*—Approximately 2 inches long by 1 inch wide when beginning to expand.

*Color.*—Apricot Yellow (Pl. IV), shading to Maize Yellow (Pl. IV), tipped with Deep Rose Pink (Pl. XII).

*Opening.*—Even.

*Peduncle.*—Relatively short, usually 4 to 6 inches, thus bringing foliage close to flower.

Bloom:

*Size when fully open.*—Medium to large, averaging 4 to 5 inches in diameter.

*Petalage.*—Usually from 40 to 50 petals.

*Color.*—The entire center is deep Apricot Yellow (Pl. IV), shading to Maize Yellow (Pl. IV) at the edges. The outer two or three rows of petals are approximately Maize Yellow edge with Deep Rose Pink (Pl. XII). This produces a general color effect of an Apricot Yellow rose surrounded by a frame of two or three rows of Rose Pink petals. The reverse side of the petals is much the same as the upper surface in coloring.

*Form.*—High centered, with outer petals imbricated and becoming loosely rolled outward while the center remains high. Only in the late stages of opening are the stamens visible.

*Fragrance.*—Tea.

*Longevity.*—Very excellent keeper. Fully open flowers when cut will last five days before petals fall.

Petals:

*Shape.*—Outer petals obovate, small inner petals spatulate. Edges undulate.

*Size.*—Average of outer petals is 1½ by 2 inches.

*Behavior.*—Persistent.

*Texture.*—Heavy.

Reproductive organs:

*Pistils.*—Few; short; Cadmium Orange (Pl. III); bunched in center of flower. Style—short. Stigma—prominent.

*Stamens.*—Many; longer than pistils and surrounding them. Filaments—about ¼ inch long and red-tinged. Anthers—large; Light Cadmium (Pl. IV).

Having thus disclosed my invention, I claim:

The new and distinct variety of hybrid tea rose plant, characterized particularly as to novelty by its exceptionally strong stems; the good, high-centered form and excellent keeping qualities of its flowers; and the novel blend of deep tones of yellow and rose of its bud and bloom, substantially as herein shown and described.

ARTHUR PRESTON HOWARD.

No references cited.